United States Patent [19]

Curry et al.

[11] 4,295,199

[45] Oct. 13, 1981

[54] AUTOMATIC FLUOROMETER AND DATA PROCESSOR FOR PERFORMING FLUORESCENT IMMUNOASSAYS

[75] Inventors: Robert E. Curry, Novato; Michael G. Simonsen, San Rafael, both of Calif.

[73] Assignee: Bio-Rad Laboratories, Inc., Richmond, Calif.

[21] Appl. No.: 86,917

[22] Filed: Oct. 22, 1979

[51] Int. Cl.³ ............................................. G01N 33/16
[52] U.S. Cl. ............................. 364/555; 235/92 PC; 250/461 B; 364/413
[58] Field of Search ............... 364/555, 413, 415, 414; 250/461 B, 458; 235/92 PC, 92 V; 424/7; 356/335

[56] References Cited

U.S. PATENT DOCUMENTS

| | | | |
|---|---|---|---|
| 3,497,690 | 2/1970 | Wheeless, Jr. et al. | 250/461 B |
| 4,006,360 | 2/1977 | Mueller | 250/461 B |
| 4,036,946 | 7/1977 | Kleinerman | 250/458 |
| 4,125,828 | 11/1978 | Resnick et al. | 250/461 B |
| 4,150,295 | 4/1979 | Wieder | 250/461 B |
| 4,153,675 | 5/1979 | Kleinerman | 250/458 |
| 4,171,956 | 10/1979 | Uzgiris | 250/461 B |

*Primary Examiner*—Errol A. Krass
*Attorney, Agent, or Firm*—Townsend and Townsend

[57] ABSTRACT

Apparatus is disclosed for quantitating relatively small amounts of a clinically significant compound which had been fluorescently tagged. The apparatus has a transparent cell for holding a prepared liquid sample (which includes fluorescent particles). A light source generates a stable light beam that is focused on the sample in the cell so that the beam causes fluorescent emissions by the particles in the sample. The intensity of the emissions is a function of the intensity of the light beam and the concentration of the fluorescent particles in the sample. A detector in optical communication with the cell receives and senses photons defining the fluorescent emissions. The number of sensed photons is counted and the total count from the sample over a fixed time period is a measure of the number of fluorescent particles in the sample. A microcomputer system is further disclosed including a primary microprocessor which is interfaced via latches and buffers on a data bus to a system memory, system pheripherals, and major system subassemblies.

44 Claims, 12 Drawing Figures

AUTOMATIC FLUOROMETER AND DATA PROCESSOR FOR PERFORMING FLUORESCENT IMMUNOASSAYS

BACKGROUND OF THE INVENTION

The present invention relates to an automated system for the immunoassay of subnanogram quantities of certain compositions by molecular fluorescence.

The quantitative determination of small amounts of clinically significant compounds, such as metabolites, hormones, drugs and proteins are of recognized diagnostic importance. Radioimmunoassay (RIA) has become the standard method for making such determinations because of its sensitivity and specificity.

However, RIA has certain drawbacks. The radioactivity associated with RIA may present psychological or physical health hazards to the technologists, requires special licensing from nuclear regulatory agencies, requires the special disposal of wastes, limits the useful life of a reagent kit to a few months at the most, and requires relatively expensive instrumentation. To circumvent these drawbacks, alternative methods including fluorescence immunoassay (FIA) have been developed.

FIA is a technique in which a fluorescent molecule is substituted for the radioactive label used in RIA. Some of the advantages of FIA are: no radioactivity, a much longer useful lifetime of the test components or chemicals necessary for the assay, and relatively less expensive instrumentation for performing the assays.

By way of background, the commonly owned co-pending U.S. patent application bearing Ser. No. 875,475, filed Feb. 6, 1978 for SOLID PHASE IMMUNOFLUORESCENT ASSAY METHOD, now U.S. Pat. No. 4,201,763, describes in detail a FIA method for antigens (or haptens) and their antibodies through the use of an immune reactant related to the antibody or antigens to be determined which is covalently bonded or coupled to polymeric particles whose size permits direct measurement of a labelled immunological reagent's fluorescence in an aqueous suspension thereof by direct optical spectroscopy. A key to the method described in that U.S. patent application lies in the selection of certain types of polymeric particles in sizes which provide a substantially homogeneous suspension during execution of the assay. It has been discovered that such a condition exists and that direct fluorometric measurements can be made when the polymeric particles have a size of about 0.1–10 microns.

Utilizing such particles, an appropriate immune reactant immunologically related to unknown antigen or antibody to be determined is covalently bonded thereto. The particles, unknown immune reactant, and appropriate fluorescently labelled immune reactant are mixed under conditions so that a quantity of the labelled immune reactant proportional to the concentration of the unknown immune reactant is immunologically bound, directly or indirectly, to the particles. The particles can then be readily physically separated and their fluorescence directly measured by fluorometry.

In accordance with said co-pending U.S. patent application, the FIA provides water insoluble hydrophilic polymeric particles of about 0.1–10 microns in size and having covalently bonded thereto the immunological homolog for an antigen or antibody to be determined. The particles are combined with the antigen or the antibody to be determined in an aqueous solution to form an immunological bond therebetween. A fluorescently labelled antigen or antibody corresponding to the antigen or antibody to be determined is immunologically bound to the particles. The particles are separated from the aqueous solution, typically by centrifuging the solution, and their fluorescence is measured in an aqueous suspension by fluorometry to obtain information from which unknown antigen or antibody can be determined.

Any suitable water insoluble polymeric particle may be utilized in the FIA described in said U.S. patent application. Generally, the particle will be in spherical or bead form and will be selected from polymers which can be derivatized to give a terminal primary amine, terminal carboxyl, or hydroxide group. The antibody or antigen is then immobilized on the particle under conventional reaction conditions to produce a covalent bond therebetween. Useful polymeric particles are formed, for example from crosslinked polyacrylamides. Other suitable polymeric particles are described in said U.S. patent application and in the references cited therein.

After the separation of the beads or particles from the aqueous solution, their fluorescence is measured in an aqueous suspension in a fluorometer on a sample by sample basis.

A key to the success of FIA is the reliability and accuracy of the fluorometer over extended periods of time. In this regard, prior art fluorometers had certain shortcomings which could affect the ultimate readout and thus compromise the accuracy of the test. Conventional fluorometers that operate in an analog mode are unsatisfactory because of the relative insensitivity of such fluorometers when measuring the low light intensities encountered when performing FIA.

Better accuracy can be attained with photon-counting fluorometers which are relatively simple and inexpensive to construct. Robert E. Curry et al discuss the construction of photon-counting fluorometers (hereinafter "fluorometer" unless otherwise indicated) in "Design and Evaluation of a Filter Fluorometer that Incorporates a Photon-Counting Detector" on pages 1259–1264 of *Clinical Chemistry*, Vol. 19, No. 11, 1973, although the use of such fluorometers in conjunction with FIA has not heretofore been considered. The Article notes that photon-counting is an effective method for minimizing dark current contributions in photomultiplier tubes since electrons emitted from the dynodes are amplified less than electrons emitted from the photocathode and level discriminating circuitry can be used to differentiate between the dark current and photon signals.

For the determination of small amounts (i.e. from subnanomolar levels up) of clinically significant compounds by FIA, accuracy problems are, of course, not fully solved by employing a photon-counting fluorometer. Stray light, a non-uniform suspension of the fluorescent beads, light scattering, a variation in the magnitude of the samples' own fluorescence as well as changes in the primary light intensity all adversely affect the ultimate readout and lessen its accuracy. In addition, existing FIA methods must rely on an essentially manual, sample by sample determination of the fluorescence which requires the constant attention of highly skilled and, therefore, costly operators. This in turn has a tendency to drive up the already high costs for such tests.

SUMMARY OF THE INVENTION

The present invention provides an apparatus for conducting FIA on an automatic, reliable, self-correcting and continuous basis for the quantitation of antigens or haptens and antibodies of any molecular weight and at concentrations from subnanomolar levels upwards. Initially, in one type of a competitive binding FIA, the antigen labeled with a fluorescent dye competes with the antigen in the sample or standard for a limited amount of antibody which is immobilized on a 0.1–10 micron polyacrylamide bead. After a suitable incubation, the labeled antigen bound to the antibody beads is separated from the free fluorescently-tagged antigen in the supernatant by centrifugation and decantation. After resuspending the antibody beads in buffer, the fluorescence bound to the beads is measured in accordance with the present invention with a fluorometer that utilizes a feedback stabilized light source which illuminates a sample in a transparent holding cell to generate fluorescent emissions. The emissions are sensed by a photon-counting detector that forms photon generated output pulses from which background noise is effectively eliminated. System electronics for the present invention employs large scale integration microcomputer architecture to provide an automated capability. In addition to supervisorial and sequencing tasks, the microprocessor performs data acquisition and data reduction operations to convert photon count information into antigen concentration. The apparatus of the present invention assures a measurement precision and accuracy of about one to three percent for the above indicated relatively low concentrations being measured.

The apparatus of the present invention is fully automated, being capable of processing one sample after the other on a continuing basis. For this purpose the fluorometer includes a sample cell which is fluidly communicated with a suitable pump that transports a predetermined sample volume into the cell, maintains the volume in the cell until its fluorescence has been measured, and thereafter replaces the sample in the cell with a new one. The pump can be operatively coupled with an automatic sample retrieving unit.

Generally speaking, the present invention provides an apparatus for quantitating relatively small amounts of a clinically significant compound such as thyroxine or triiodothyronine which has a transparent cell for holding a prepared liquid sample. A light source generates a stable light beam that is focused on the sample so that the beam causes fluorescent emissions by the particles in the sample. The intensity of the emissions is a function of the intensity of the light beam and the concentration of the fluorescent particles in the sample. A detector in optical communication with the cell receives and senses photons defining the fluorescent emissions by the particles when excited by the light beam. The number of sensed photons is counted and the total count from the sample (over a given time period) is a measure of the number of fluorescent particles in the sample.

The associated optics include a lens which focuses the light beam on the sample, a band pass filter which eliminates substantially all light from the light beam other than light having a wavelength which excites the particles and generates fluorescent emissions, and a heat absorbing filter in the optical branch between the light source and the sample. The branch of the optics between the sample and the detector includes a collecting lens, a cutoff filter to remove the excitation wavelength and thereby the effects of incoming light scattered by the sample, and a band pass filter which removes from the light received by the detector substantially all wavelengths other than the wavelength at which the particles fluoresce. The sample, the light source as well as the optics are mounted within a black housing which includes suitable light traps to prevent light scattering, secondary fluorescent emissions, etc. As a result, the detector receives substantially only fluorescent emissions caused by the light beam striking the fluorescent particles in the sample to assure that the emission, and in particular the photons of the emissions are the result of fluorescence caused by the light beam only. This significantly enhances the accuracy of the photon count by the detector.

To prevent fluctuations in the photon count due to changes in the intensity of the light beam the light source is stabilized. For this purpose, a photosensor such as a silicon photodiode is mounted proximate the sample cell and downstream of the optics in the branch of the optics between the light source and the cell. A variation in the light beam intensity sensed by the photodiode is used to correspondingly increase or decrease the voltage of the power source for the light source so as to maintain the light beam intensity constant and at a predetermined level. Consequently, variations in the light beam intensity due to fluctuations in the power supply voltage, the age of the light source and the like are prevented from affecting the fluorescent emissions by the particles in the sample being tested.

The detector itself is a photomultiplier, preferably a photomultiplier tube which generates an output charge or signal pulse in response to each photon sensed by the tube. The construction of such photomultiplier tubes is well known. Suffice is to say that the output of the tubes includes noise caused by thermal electrons emitted by the dynodes of the tube and which produce corresponding noise pulses at the output side. The noise pulses have an amplitude significantly lower than the amplitude of the charge pulses caused by the sensed photons. To prevent the noise pulses from affecting the ultimate photon count a discriminator eliminates from the count pulses of an amplitude less than a predetermined minimum, e.g. less than about the amplitude of the noise pulses. The photon pulses are passed to appropriate counting electronics such as cascaded BCD counters.

As a consequence of the foregoing, the ultimate photon count is highly accurate and is typically within a range of one to three percent, which is fully within acceptable limits for FIA.

The present invention further fully automates the placement of samples in the sample cell and their replacement with fresh samples while assuring a complete rinsing of the cell and associated fluid conduits to prevent one sample from affecting the photon count of the next.

In this regard, the present invention contemplates to form a hollow sample cell in a transparent, e.g. quartz housing having a generally square (or rectangular) crosssection with corresponding perpendicular sides. One side faces and is perpendicular to the incoming light beam and another one faces the photomultiplier and is perpendicular to the fluorescent emissions received thereby. The housing includes a sample inlet and a sample outlet connected with a sample source, e.g. a sample retrieving probe and a sample discharge point, e.g. a container which receives tested samples as waste for subsequent disposal. The probe is connected to the cell housing inlet via an inert conduit such as flexible Teflon tubing. The outlet of the cell housing is connected to the discharge point via a readily flexible hose. A pump is located between the outlet and the discharge point and preferably comprises a peristaltic pump which conventionally acts on the flexible hose so that the sample is drawn by suction from the probe into the cell and is not subjected to the potentially damaging mechanical action of a pump. Preferably, the sample probe is alternatingly inserted in a sample holder and a rinse solution holder. In this manner, the sample cell and the intake tubing are rinsed before a new sample is drawn into the cell to assure that all remnants of the previous sample are removed before the fresh sample is introduced.

The present invention further appropriately sequences the operation of the pump so that a fresh sample is intermittently drawn into the cell and is stationarily maintained in the cell for the necessary time period to measure its fluorescence, typically about two seconds. Thereafter, the tested sample is withdrawn, the cell is washed with a rinse solution and filled with a fresh sample for measuring it fluorescence. Thus, the entire process is automated and the need for constant supervision of the device by a skilled operator is eliminated.

The microcomputer system of the present invention includes a primary microprocessor (hereinafter sometimes simply "processor" or "microprocessor") which is interfaced via appropriate latches and buffers on a data bus to system memory, system peripherals, and major system subassemblies. In particular, the primary processor communicates with the counting electronics, appropriate sequencing electronics controlling the sample retrieval apparatus, and a separate arithmetic processor. Additionally, the processor communicates with keyboard switches, electronics controlling a display and a keyboard, and an interface that permits data transfer to a remote computer. The sequencing electronics may itself comprise a dedicated microprocessor to simplify the primary processor's communication with the sample retrieval apparatus.

Fluorescence information regarding a particular sample within the sample cell is accomplished by a counting sequence wherein the primary processor initially clears the counting electronics and then enables the counters for a period determined by a software loop of a fixed number of machine cycles, the machine cycle duration being precisely fixed by the processor's crystal controlled clock. Counting is monitored by the processor, and a multi-digit count is determined and stored in system memory for subsequent processing.

Prior to counting the fluorescence of actual samples, the fluorescence of a number of say 10 to 12 standard samples is measured and the microprocessor computes a doseresponse curve for one or more and preferably for four data reduction techniques, to wit a linear interpolation, a logitlog, hyperbolic and reciprocal program and retains in memory the standard curve parameters for the reduction technique that gives the best regression coefficient. For thyroxine or triiodothyonine that coefficient is typically in excess of 0.990 for the logit function. With the dose-response curve computed, the fluorescence of each of the samples is measured and the concentration of antigen in the sample is computed and printed out. This is accomplished on a continuing basis until all samples in a given set have been measured.

DESCRIPTION OF THE PREFERRED EMBODIMENTS

Figure 1:
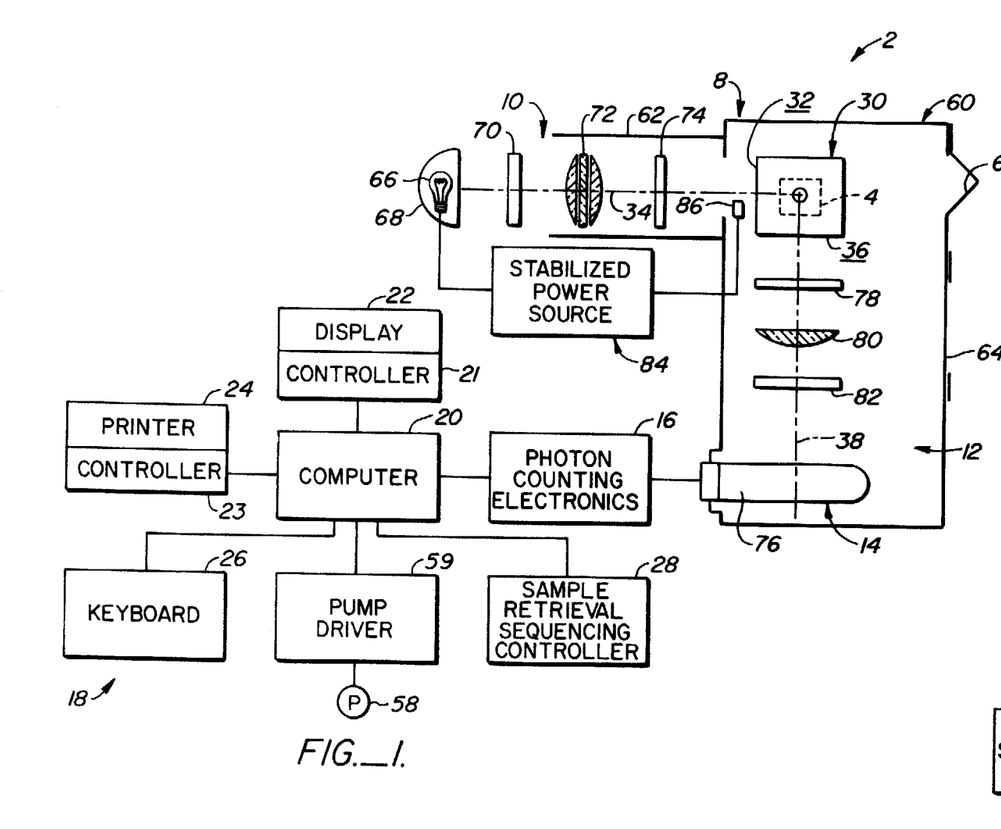
FIG. 1 is an overall, schematic illustration including a more detailed illustration of the fluorometer of a fluorescence immunoassay apparatus constructed in accordance with the present invention.
Figure 2:
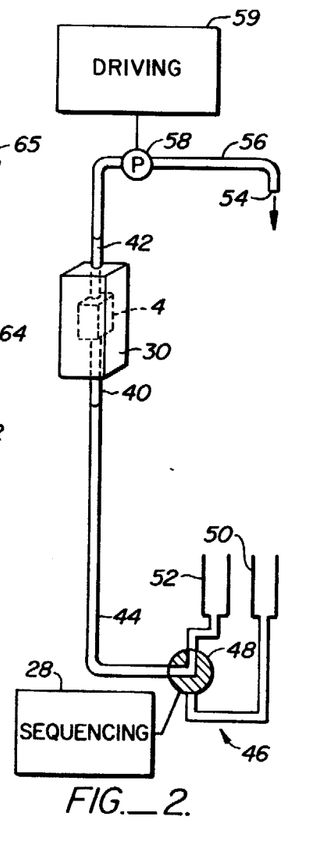
FIG. 2 is a schematic sample flow diagram including the transparent sample holding cell constructed in accordance with the present invention.

Referring first to FIGS. 1 and 2, an apparatus 2 constructed in accordance with the present invention for performing fluorescent immunoassays and in particular for quantitating relatively small amounts of a clinically significant composition such as thyroxine, for example, comprises a sample holding cell 4 which forms part of a flow system 6; optics 8 including a first optical branch 10 for subjecting the sample in the cell to a beam of light and a second optical branch 12 for collecting fluorescent emissions generated by fluorescing particles in the sample when excited by the beam; a photon detector 14 including photon counting electronics 16 which receives the fluorescent emissions from the sample in the cell; and system electronics 18 for appropriately analyzing the photon count for each sample as is more fully discussed below and for sequencing the various operations performed by the device.

System electronics 18 includes a microcomputer 20, a display controller 21 for interfacing to a visual display panel 22, a printer controller 23 for interfacing to a printer 24, a keyboard 26 for inputting various data and commands, and sequencing control electronics 28 controlled by microcomputer 20 for initiating and terminating various functions of the apparatus. To facilitate the understanding of the invention, the subfunctions and subsystems of the apparatus will be individually discussed before the overall operation of the apparatus is described in detail.

The sample flow system 6 comprises as its central part a flow housing 30 constructed of an optically pure, transparent material such as quartz and which has a square cross-section as is best seen in FIG. 1 to form four mutually perpendicular sides including a first side 32 which is perpendicular to the optical axis 34 of the first optical branch 12 and a second side 36 which is perpendicular to the optical axis 38 of the second optical branch 12 (and which is also perpendicular to the first optical axis 34). The housing defines sample cell 4 which also has square cross-sections and which has flat interior walls that are parallel to the exterior sides of the housing. An inlet 40 of the housing is connected to a length of preferably flexible intake tubing 44 constructed of a chemically inert material such as polytetrafluoroethylene (Teflon).

The other end of the intake tubing fluidly communicates with a sample probe 46. The sample probe may be a hollow, movably mounted tube (not separately shown) which can be immersed in containers holding differing solutions. Since the probe does not form a part of the present invention, it is simply illustrated as comprising a valve 48 which alternatingly fluidly communicates the intake tubing 44 with a first container 50 holding a sample to be analyzed and a second container 52 holding a rinsing solution. Additional containers may be provided to allow a plurality of samples to be analyzed.

The outlet 42 of the cell housing communicates with a point of discharge 54 (which may comprise a waste solution bottle or container, not separately shown) via a discharge hose 56 made of a readily and repeatedly compressible material, such as Tygon tubing. Since only waste materials flow through the discharge hose, it need not be constructed of inert material.

A pump 58 is placed downstream of the sample housing 30 and draws the sample or the rinse solution from the appropriate container into the sample cell 4 by suction. Direct contact between the pump and the fresh sample and potential mechanical damage to the sample constituents are thereby prevented. Preferably, the pump comprises a conventional peristaltic pump which engages the outer surface of the discharge hose 56. Pump 58 is controlled by computer 20 through appropriate pump driving circuitry 59 which may include a transistor switch and a relay.

The sample housing 30 is disposed in a generally L-shaped, optical chamber 60 at about the intersection of the perpendicular chamber legs 62 and 64, so that the center of the flow cell 4 is at the intersection of the perpendicular optical axes 34, 38 which also positions housing sides 32, 36 perpendicular to the respective optical axes.

The other end of the first optical branch 10 is defined by a light source 66. Preferably, the light source comprises a 50 W tunsten halogen lamp provided with a parabolic reflector 68. In the optical train between the light source and the sample cell are a heat absorbing filter 70, a condensing lens 72 and a narrow band pass or interference filter 74. For instances in which the fluorescent is fluorescein (which has an excitation wavelength of 490 nanometer (nm) and an emission wavelength of 520 nm) the band pass filter 74 comprises a 490 nm narrow branch pass interference filter.

The second optical branch 12 terminates in a photomultiplier tube 76 (PMT) disposed in the optical chamber leg 64 opposite the second sample housing side 36. Disposed between the sample housing and the PMT are a cutoff filter 78 made of low fluorescence glass to block the excitation wavelength, a collecting lens 80 and a narrow band pass filter 82. For the above-discussed fluorescent the cutoff filter is a 515 nm cutoff filter to prevent scattered excitation light from reaching the PMT while the band pass filter is a 520 nm narrow band pass interference filter to isolate the emission wavelength and limit the light reaching the PMT to the emission wavelength.

To eliminate stray light and light reflections which can directly or indirectly adversely affect the photon count by the PMT 76, the interior of housing 60 is black. Further, a light trap 65 is provided in the form of a well or depression formed in the housing wall at the extension of the first optical axis 34. The light trap prevents light which passes through cell housing 34 from being reflected back into the cell (and thereby causing secondary fluorescent emissions) and from being reflected into the second optical branch 12 where it could affect the photon count by the PMT.

As should be apparent, upon energizing light source 66 light of the excitation wavelength, e.g. 450 nm is focused onto the sample in cell 4 and stimulates the fluorescing particles in the samples to generate fluorescent emissions of a predetermined wavelength, e.g. 520 nm. The fluorescent emissions propagate in all directions equally and those propagating along the second optical axis 36 are focused onto the cathode (not separately shown) of the PMT 76. In the preferred embodiment, the PMT is a nine-stage, side-on type PMT specifically adapted for photon counting. It operates with a cascade effect in which an electron emitted by the photocathode due to an impinging photon is accelerated to the first dynode (not separately shown) of the PMT by a high voltage bias where it generates a number of secondary electrons. The number of secondary electrons is a function of the bias voltage and the dynode material and structure. The secondary electrons are then accelerated to the second dynode where each generates a number of additional secondary electrons. The process continues down the dynode chain to the anode of the PMT, thereby producing a large current amplification.

Quantitatively, the fluorescent emissions of the excited sample in cell 4 are a function of the intensity of the excitation light beam from light source 66 and the concentration of fluorescent particles in the sample or, since the cell volume is fixed, the total number of fluorescent particles in the sample cell. Thus, any fluctuation in the intensity of the excitation light beam would result in a corresponding change in the intensity of the fluorescent emissions and cause an error which is a function of the intensity change in the excitation beam. Since the overall accuracy of the apparatus of the present invention should not deviate by more than three percent variations in the excitation beam intensity in excess of one percent from normal are to be avoided. Light beam intensity changes in excess of one percent are frequently encountered because of fluctuations in the line voltage, intensity changes due to the age of the light source and the like. To prevent these from affecting the charge pulse count from the PMT 76, the present invention provides the light source stabilization circuit 84 illustrated in FIG. 3.

Figure 3:
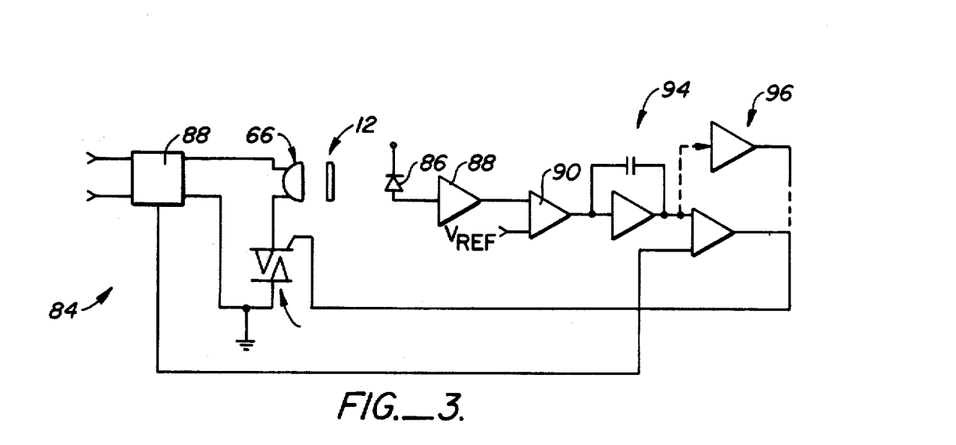
FIG. 3 is a schematic of the stabilization circuit for the fluorometer light source.
Figure 4:
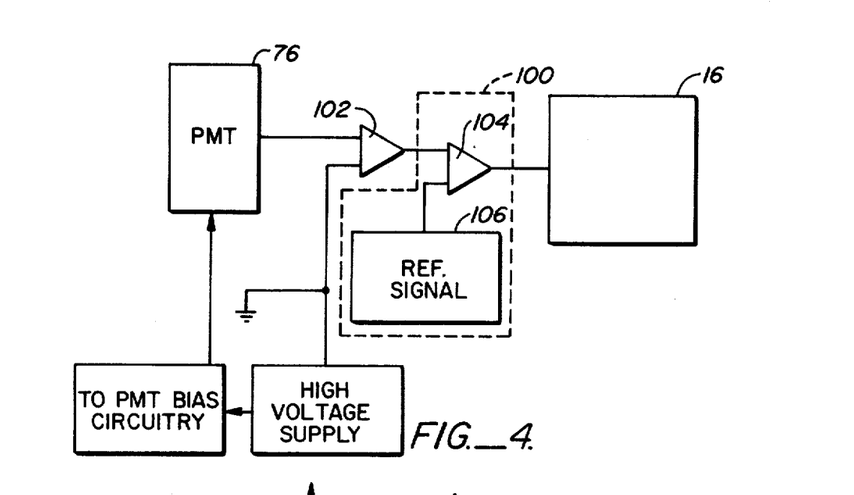
FIG. 4 is a schematic of the discriminating circuit of the present invention.

Referring now to FIGS. 1 and 3, a silicon photodiode 86 is positioned in the optical branch 10 immediately adjacent flow housing 30, that is optically downstream of heat absorbing filter 70, condensing lens 72 and band pass filter 74, so that light focused onto the sample cell 4 is also sensed by the photodiode. The photodiode operates in the photoconductive mode and its output is amplified in a preamplifier 88, the output of which is compared to a preset reference voltage $V_{ref}$ in a comparator 90. The reference voltage may be obtained from a precision voltage divider comprising a resistor and a trimmer potentiometer (not separately shown) and, once set, it is typically not changed. The comparator output is then used to modulate a triac 92 for the light source to maintain the intensity of its light beam constant.

In a preferred embodiment of the invention, the comparator senses the error voltage and forms as an output either +10 V or −10 V, depending on the error voltage, which is sent to an integrator 94. The integrator ramps in the appropriate direction to adjust a triac switching reference voltage. The switching reference is inverted to obtain both a positive and a negative switching reference. This bipolar reference is applied to a pair of triac drivers 96 along with the attenuated 24 V.A.C. output of transformer 98. During each half cycle of the A.C. wave form, the triac is off until the A.C. voltage exceeds the switching reference level. When the A.C. voltage swings above the reference level, the triac is gated on and conducts until the A.C. voltage falls back below the reference. In this manner, the duty cycle of the light source A.C. power input is modulated to maintain its output constant.

With a constant excitation beam the fluorescent emissions for a given sample in cell 4 remain likewise constant. Referring now to FIGS. 1, 4 and 5A-C, to maximize the sensitivity of detector 14, the detector operates in a photon counting mode in which an individual charge or signal pulse is produced by the PMT 76 for each photon which reaches the PMT's photocathode (not separately shown). The PMT operates in this mode for light levels of between about $10^{-11}$ to $10^{-13}$ W.

Figure 5A:
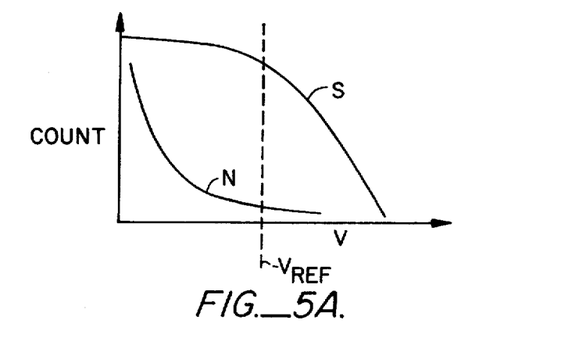
FIGS. 5A–C are diagrams which illustrate the conditioning of the output signals of a photomultiplier by the circuit shown in FIG. 4.

Thermal electrons are also emitted by the dynodes and they produce noise pulses at the anode which constitute an undesirable noise component which can adversely affect the signal pulse count. The noise pulses have a substantially lesser amplitude than the photon generated signal pulses and to eliminate them, a discriminator 100 precedes the photon counting electronics 16. As is illustrated in FIG. 5A, the noise component of the signal is relatively large at low voltages and relatively small at higher voltages. To eliminate most the noise pulses, a reference voltage $V_{ref}$ is chosen at a level at which the signal count S is relatively high and the noise count N is relatively low as is indicated in FIG. 5A.

Figure 5B:
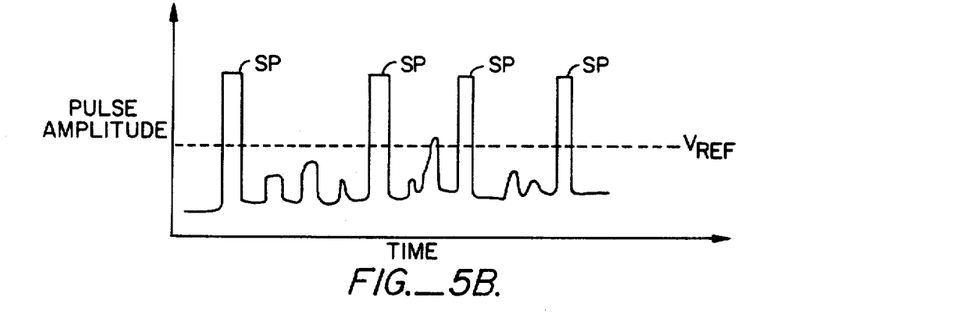
Figure 5C:
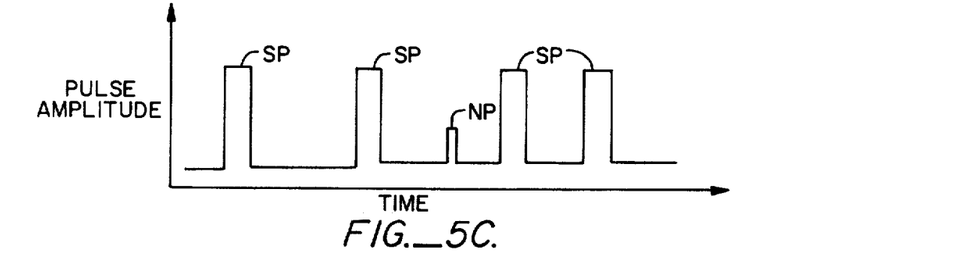

Both noise and signal pulses are amplified in an amplifier 102 and the amplifier output is fed to a comparator 104 which acts as an amplitude discriminator and receives as its second input a preset reference signal from an appropriate source 106. The comparator eliminates all pulses having an amplitude less than $V_{ref}$ as is indicated in FIG. 5B and thus yields an output signal which essentially comprises only signal pulses SP while all noise pulses NP (except for one illustrated in FIGS. 5B and 5C) have been eliminated.

The reference voltage $V_{ref}$ of the comparator 104 is typically preset to provide the optimum signal to noise ratio for the PMT-amplifier-comparator combination by blocking the majority of noise pulses while passing most of the charge pulses. If desired, it can also be continually adjusted by appropriately selecting the optimal $V_{ref}$ level at which the signal pulse to noise pulse is greatest. The output from the comparator, namely the signal pulses are fed to the counting electronics 16.

Figure 6:
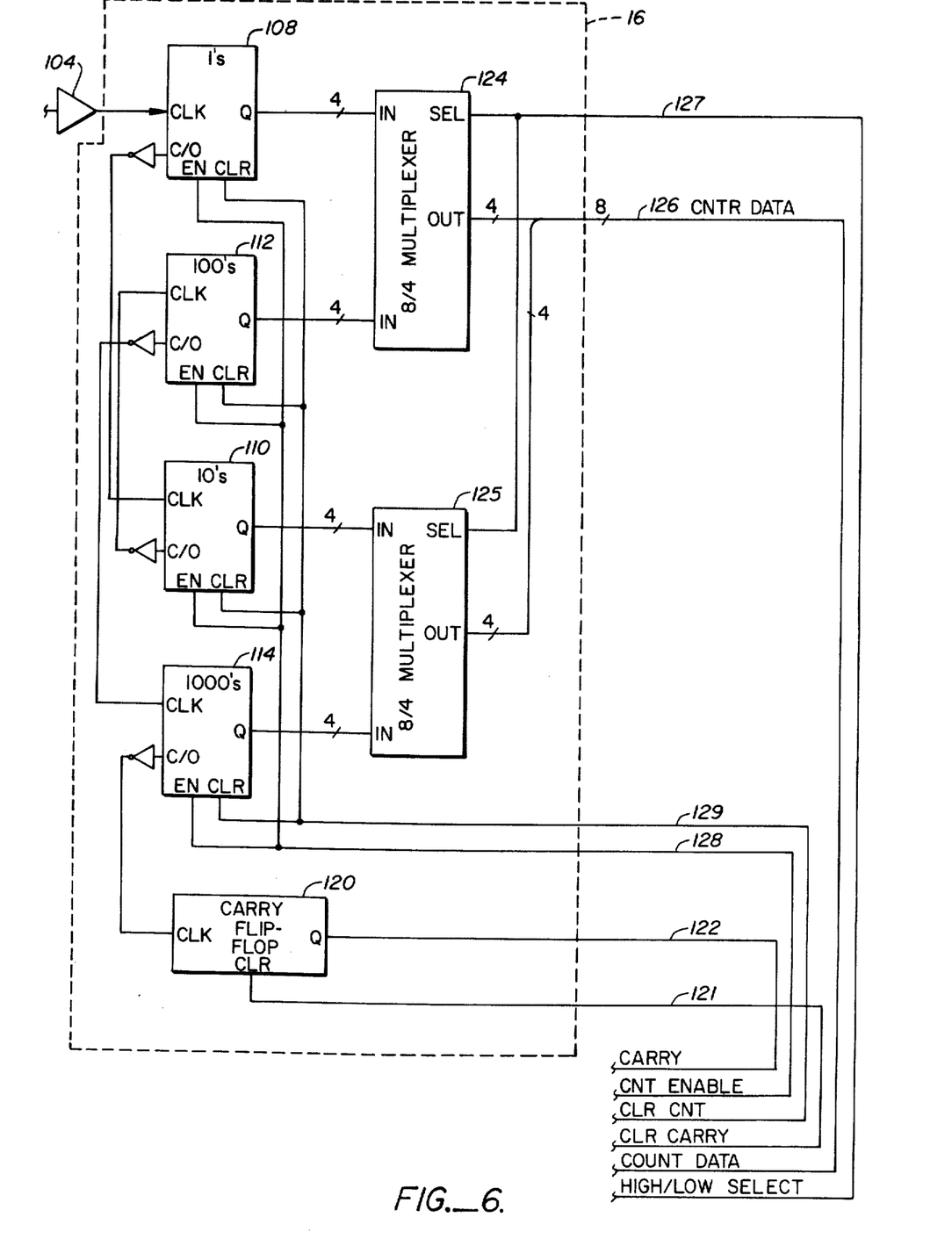
FIG. 6 is a schematic of the photon pulse counting circuit of the present invention.

Referring to FIG. 6, in a preferred embodiment of the invention, counting electronics 16 comprises four cascaded four-bit BCD counters 108, 110, 112, and 114. Each counter has a clock input, designated CLK, a carry output, designated C/O, and a 4-bit data output, designated Q. The output from comparator 104 communicates through a buffer to the input of counter 108; the carry output of counter 108 communicates through a buffer to the input of counter 110; the carry output of counter 110 communicates through a buffer to the input of counter 112; the carry output of counter 112 communicates through a buffer to the input of counter 114; and the carry output of counter 114 communicates to the clock input of a "carry" flip-flop 120. Flip-flop 120 has a clear input, designated CLR which may receive signals from microcomputer 20 on a line 121. The output of flip-flop 120, designated Q, communicates to microcomputer 120 via a line 122. The outputs of counters 108 and 112 are communicated to the inputs of an 8-to-4 multiplexer 124. Similarly the outputs of counters 110 and 114 are communicated to the inputs of an 8-to-4 multiplexer 125. The 4-bit outputs of multiplexers 124 and 125 together form an 8-bit data line 126. Multiplexers 124 and 125 have respective select inputs, designated SEL, which are tied together and receive signals on a line 127. Each counter also has an enable input, designated EN, to enable counting, and a clear input, designated CLR, to zero the counter contents. The enable inputs are tied together and receive signals from microcomputer 20 on a line 128. The clear inputs are tied together and receive signals on a line 129.

Figures 7, 7A:
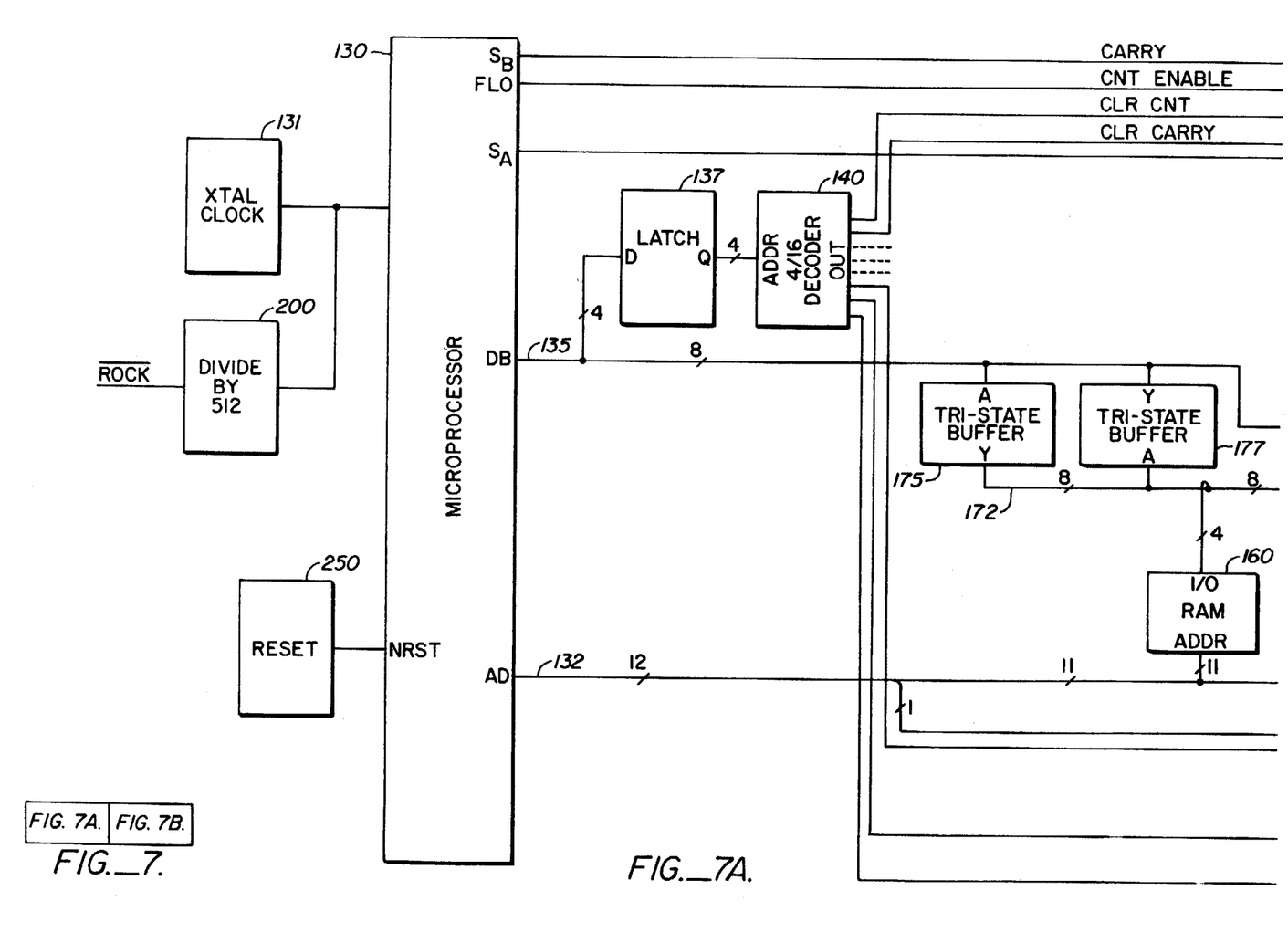
FIG. 7 is a diagram which illustrates the connection between FIGS. 7A and 7B.
FIGS. 7A–B, taken together, form a simplified circuit schematic of the microcomputer system of the present invention.
Figure 7B:
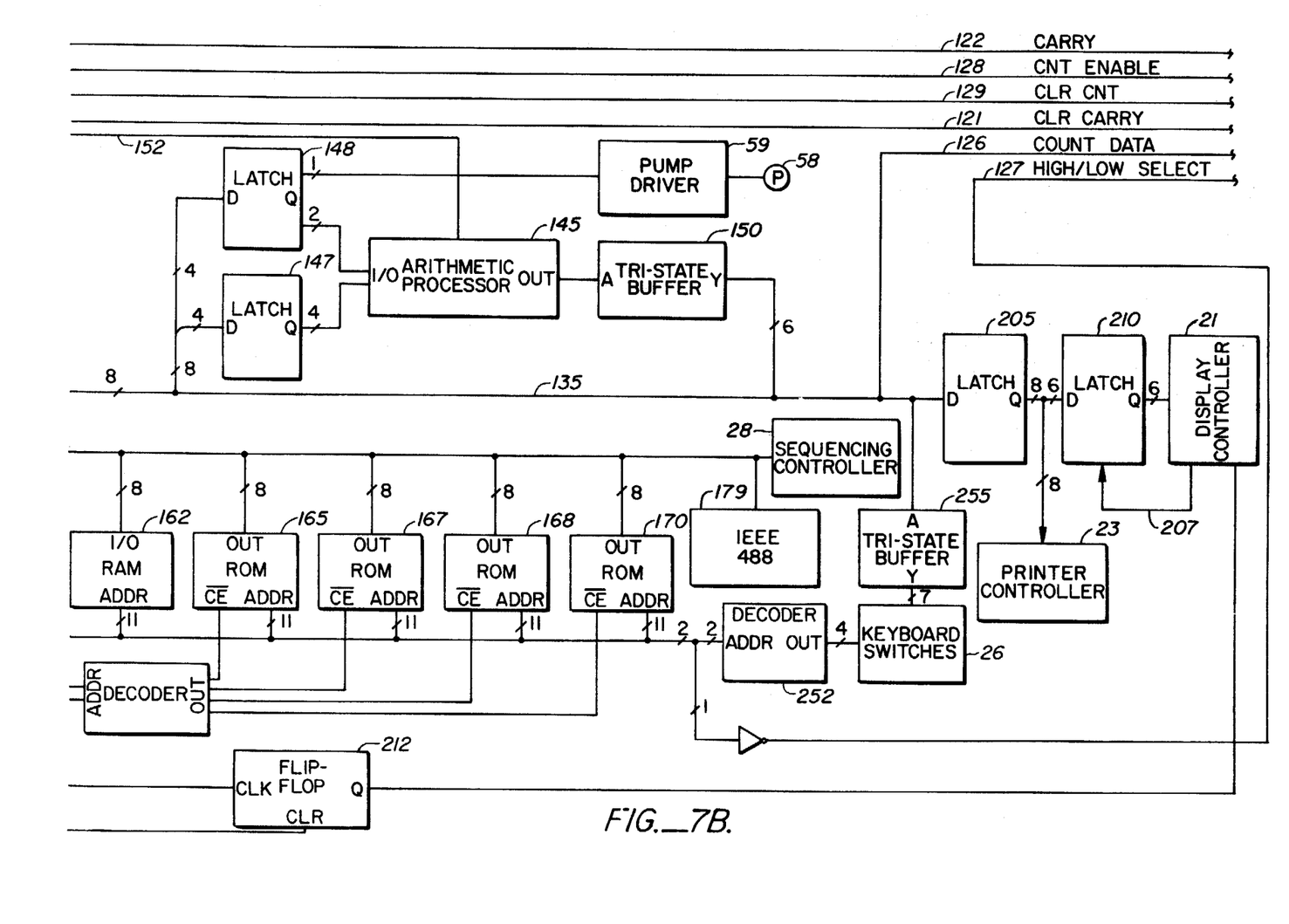

FIGS. 7A and 7B, taken together, form a system block diagram of system electronics 18 that controls the operation of the present invention. A table of preferred component types will be set forth below. The central component of the system electronic circuitry is a primary microprocessor 130 which interfaces to system memory, peripherals, and other subassemblies as will be described below. Microprocessor 130 is driven by a 4 MHz crystal clock 131. Microprocessor 130 communicates to other portions of the electronics via a 12-bit address bus 132 (designated AD0-AD11) and an 8-bit system data bus 135 (designated DB0-DB7). Data bus 135 is time multiplexed so that it carries high order address and status information during a first portion of the microprocessor execution cycle and data during the latter portion of the cycle. The high order address information (designated AD12-AD15) is latched at a quad-D flip-flop 137 by the NADS processor strobe and used to drive a 4-to-16 decoder 140 for selecting a particular device (memory unit, peripheral, etc.) for input or output. Some of the decoder outputs are used as strobes to actuate various system functions while other strobes originate directly at microprocessor 130. In addition, a number of logic gates, not shown, are used to coordinate such strobes with other status information in order to achieve correct device selection and control. Thus, address bus 132 provides microprocessor 130 with 12 dedicated address lines (designated AD0-AD11) which, in conjunction with the 4 bits latched by flip-flop 137, provide a total of 16 address lines.

Microprocessor 130 has self-contained inputs and outputs for control of peripheral devices. The outputs consist of three flags (designated FL0, FL1, FL2) and a serial port intended for serial data communication. The inputs consist of two sense inputs (designated $S_A$ and $S_B$) and a serial in port which is not used. Microprocessor 130 is interfaced to an arithmetic processor 145 by two quad D input latches 147 and 148 and a 6-bit tri-state output buffer 150. The interface is a synchronous. Arithmetic processor 145 provides an interrupt signal on a line 152 to sense input $S_A$ of microprocessor 130 in order to allow microprocessor 130 to respond to arithmetic processor 145 during execution of a mathematical operation. One of the outputs of latch 148 communicates to pump driving circuitry 59 for activating pump 58.

System memory comprises random access memory units 160 and 162 (hereinafter sometimes RAM's) that together provide 1024 8-bit bytes of read/write memory, and read-only memory units 165, 167, 168, and 170 (hereinafter sometimes ROM's) that together provide 8192 bytes of read-only memory. The system memory units are coupled directly to address bus 132, and are coupled to a memory interface data bus 172 which is coupled to system data bus 135 through bidirectional tri-state buffers 175 and 177, the operations being controlled by the NRDS and NWDS strobes of microprocessor 130. Bus 172 also communicates to sequencing circuitry 28 to allow microprocessor 130 to control sample retrieval. Sequencer 28 is selected by appropriate control lines from decoder 140 and associated logic gates in addition to the NWDS and NRDS strobes. Sequencing circuitry 28 may itself by microprocessor controlled. Bus 172 also connects to an IEEE 488 interface card 179 which allows the apparatus of the present invention to communicate to a central computer which could accumulate data from multiple instruments for statistical or other purposes.

Microprocessor 130 is interfaced directly to photon counting electronic circuitry 16 via 1-bit data lines 121, 122, 127, 128, and 129, and 8-bit data line 126. Line 126 carrying counter data is coupled to processor data bus 135 while carry line 122 is coupled to sense input $S_B$. Counter clearing line 121 and carry clearing line 129 are coupled to respective outputs of decoder 140, count enabling line 128 is coupled to flag FL0, and data select line 127 is coupled to address line AD0 of address bus 132. Thus, the numerical contents of the BCD counters and the state of the carry flip-flop may be read by microprocessor 130, and signals may be sent in order to clear the counters, clear the carry flip-flop, and enable the counters.

Microprocessor 130 communicates with display 22 through appropriate multiplexing circuitry in display control circuitry 21. Microprocessor 130 and display controller 21 are synchronized by a 7.8 kHz derivative of microprocessor clock 131 provided by a divide by 512 network 200 which drives the display multiplexing circuitry. Display 22 is capable of displaying 16 5×7 dot matrix alphanumeric characters which are refreshed at the rate approximately 70 Hz. Data for the display, consisting of 16 sequentially output ASCII characters, is stored in RAM's 160 and 162 and subsequently read out onto data bus 135 and latched by microprocessor 130 at a latch 205. The display circuitry then accesses this data by strobing a count update line 207 to transfer the data latched at latch 205 to a latch 210. Blanking of the display is controlled by a flip-flop 212 which in turn is controlled by strobes from decoder 140.

Microprocessor 130 interfaces a printer 24 through appropriate printer controller circuitry 23. The printhead of printer 24 is an impact dot matrix type utilizing seven solenoid actuated strikers and a motor-driven carriage to move the solenoids across the paper. Paper feed is accomplished by a feed solenoid and friction drive to provide a print speed of 2.3 lines per second. The printer control circuitry is preferably microprocessor based and receives ASCII input data into a 20-position buffer and then controls the motor drive and solenoid firing to form the corresponding characters. Six data lines for ASCII characters, a "print out" line and a "feed out" line for printer control circuitry 23 are coupled to the output of latch 205.

Figure 8:
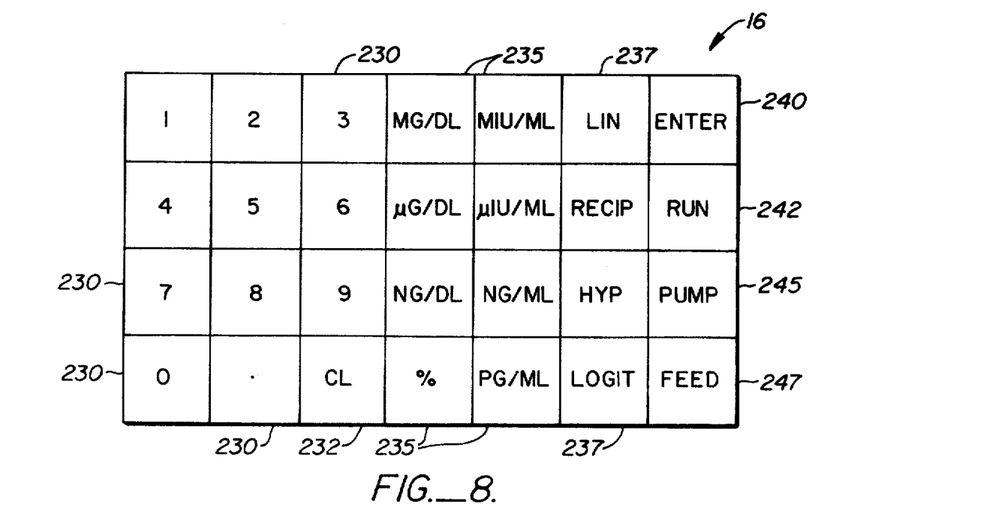
FIG. 8 is a plan view of the keyboard, illustrating the various key functions.

FIG. 8 is a plan view illustrating keyboard 16. Keyboard 26 consists of an array of 28 printed circuit mountable switches arranged as seven columns by four rows. The switches are of the mechanical contact type and are hermetically sealed at the front panel of the instrument by a rubber gasket to prevent leakage of spilled fluids into the instrument. The keyboard switches are used by the operator to enter assay parameters, standards concentrations, and to execute system commands. In particular, keyboard 16 comprises 11 numeric keys 230 (0-9 and decimal point), a clear key 232, 8 concentration units keys 235 (mg/cl, $\mu$g/dl ng/dl, %, miu/ml $\mu$iu/ml, ng/ml, and pg/ml), four mathematical reduction keys 237 (linear interpolation, reciprocal, hyperbolic, and logit-log), and four system command keys consisting of an ENTER key to 240, a RUN key 242, a PUMP key 245, and a FEED key 247. A "reset" switch is mounted at a separate front panel location and communicates to reset circuitry 250 for providing a reset pulse to microprocessor 130. Two high order lines of address bus 132 communicate to a decoder 252 which supplies four output lines corresponding to the four rows. Seven lines corresponding to the seven columns communicate via a tri-state buffer 255 to processor data bus 135. Thus, the keyboard is scanned by sequentially addressing each keyboard row with a low strobe from decoder 252. Presence of a closed keyboard switch is detected by enabling buffer 255 and reading the keyboard columns. A low on a given line into buffer 255 indicates closure of a switch in the corresponding column while the specific row of that column is determined by the status of the two address lines input to decoder 252.

While many types of integrated circuit components could be used, preferred components are set forth in the following table, designated Table I.

TABLE I

| Reference Numeral | Description |
|---|---|
| 102 | OP AMP BI-FET LH0062CH |
| 104 | Comparator LM360H |
| 108 | Decade Counter 74LS160N |
| 110 | Decade Counter 74LS160N |
| 112 | Decade Counter 74LS160N |
| 114 | Decade Counter 74LS160N |
| 120 | JK Flip-flop 74LS73N |
| 124 | Quad 2-Data Selector/Multiplexer 74LS257N |
| 125 | Quad 2-Data Selector/Multiplexer 74LS257N |
| 130 | Microprocessor 8-bit INS8060 |
| 137 | Quad Latch 74LS75N |
| 140 | 4-to-6 Decoder/Demultiplexer 74LS154N |
| 145 | Processor 6-bit MM57109 |
| 147 | Quad Latch 74LS75N |
| 148 | Quad Latch 74LS75N |
| 150 | Hex Buffer 74LS365N |
| 160 | 1024x4K Static RAM P2114 |
| 162 | 1024x4K Static RAM P2114 |
| 165 | 2048x8 EPROM B2716 |
| 167 | 2048x8 EPROM B2716 |
| 168 | 2048x8 EPROM B2716 |
| 170 | 2048x8 EPROM B2716 |
| 175 | Octal Buffer 81LS95N |
| 177 | Octal Buffer 81LS95N |
| 205 | Latch 74LS273N |
| 210 | Latch 74LS273N |
| 212 | JK Flip-flop 74LS73N |
| 252 | Decoder 74LS138N |
| 255 | Octal Buffer 81LS95N |

The software for the operation of microprocessor 130 resides in read-only memory units 165, 167, 168, and 170, and is organized into two major subsets. The first subset comprises operating procedure instructions including a main program for executing a standard assay sequence and subroutines for scanning keyboard 26, strobing display 22, operating printer 24, performing the count sequence, and operating pump 58. The second subset comprises data reduction procedures to be described in detail below.

The standard assay sequence includes a calibration sequence and a sample sequence. Prior to counting the fluorescence of actual samples, the fluorescence of a number of standard samples of known concentration is measured and a dose response curve is calculated. Thereafter, for the measured fluorescence of a sample, the antigen concentration is calculated and printed out.

Turning first to the operation of the device with respect to acquiring the fluorescence count for a given sample (standard or actual), the operation of the device may be described as follows. To briefly summarize it, the operation commences with computer 20 instructing sequencer 28 to operate valve 48 to connect the intake tubing 44 with sample container 50. The computer then energizes pump 58 long enough so that a sufficient volume of the sample from the container 50 is drawn (by vacuum) through the intake tubing 44 to completely fill sample cell 40 in sample housing 30. The computer than de-energizes the pump.

With the light source 66 energized, the fluorescent particles in the sample cell 4 fluoresce and emit fluorescent emissions some of which are directed onto PMT 76. Photodiode 86 and stabilizing circuitry 84 maintain the intensity of the light beam from source 66 constant.

The fluorescent emissions received by the PMT result in a bombardment of the PMT cathode (not separately shown) by photons with each photon resulting in a charge or signal pulse. The discriminator circuit 100 removes from the output of the PMT relatively low amplitude noise signals so that the output from the discriminator circuit comprises substantially only signal pulses with each pulse representing a fluorescent emission photon received by the PMT cathode. These pulses are fed into BCD counter 108.

Microprocessor 130 commences the counting sequence by sending low going strobes on carry clearing line 121 and counter clearing line 129 in order to clear the counters and the carry flip-flop. Microprocessor 130 then sets FL0 high in order to communicate a high signal on counter enabling line 128 to enable the counters and begin the count period. The duration of the count period is determined by a software loop of a fixed number of machine cycles; the machine cycle time being precisely fixed by crystal controlled clock 131. During the count period, microprocessor 130 periodically checks carry flip-flop 120, and if a carry occurs, the microprocessor increments a carry storage register in memory and clears the flip-flop. At the end of the count period, FL0 is set low to stop the count. Microprocessor 130 then reads this data through multiplexers 122 and 125 and adds it (4 BCD digits) to the number of carries multiplied to 10,000 to obtain the total number of counts during the count period. Counting continues for an exact, constant predetermined length of time, say two seconds as determined by the processor clock. At the end of the two second time period, counting is discontinued and the total count is further processed as is described below.

During or immediately after the photon count, sequencer 28 switches valve 48 of the sample probe 46 so as to connect the intake tubing 44 with rinse solution container 52. Upon the termination of the photon count computer 20 energizes pump 58 again which now draws rinsing solution into the intake tubing. The pump remains energized until at least the entire sample cell 4 is filled with rinsing solution. Drawing the rinsing solution into the sample cell causes the discharge of a corresponding volume of already tested sample fluid through the discharge hose 56 to discharge point 54 and, for example, into an appropriate waste fluid container (not shown). Once the sample cell is filled with rinsing solution, valve 48 again fluidly connects the sample container 50 with intake tubing 44. Pump 58 may continue to operate or may be de-energized until the operation of the valve has been completed. Thereafter, the pump draws a fresh sample into the sample cell 4 as above-described, while a corresponding volume of the rinsing solution is discharged via the discharge hose. Of course, the original sample in container 50 will have been replaced with a fresh sample or a new sample container will have replaced the original one unless it is desired to test the same sample twice.

Having described the operation of aspirating and measuring the fluorescence of a given sample, the overall operation of the apparatus by the operator may be understood. Operation of the apparatus in order to carry out a standard assay procedure is best understood with prior reference to the key functions of the various keys illustrated in FIG. 8.

Numeric keys 230 are used to key in numeric assay parameters (precision and multiplicity) and standards values. The maximum number of digits or alphanumeric characters which may be entered is 14. The numerial "1" key performs a special function which allows the user to halt the system during the run. In order to achieve this function the user must depress and hold the numerial "1" during printout of either the standards results or a sample result. The system scans the keyboard immediately following the printout sequence. The system remains stopped until RUN key 242 is depressed.

CLEAR key 232 is used to erase values from the system memory, if a keying error is made. When CLEAR key 232 is depressed and released, the display and corresponding active location in system memory are cleared to 0. Number entry may then be corrected by depressing the appropriate numeric and concentration keys. Clear key 232 may also be used in a memory modification procedure to delete a bad point from the standard curve by clearing the corresponding data from the system memory.

Concentration units keys 235 are used to key in concentration units during entry of standards values. When the user depresses the key labeled with a particular concentration unit appropriate for the assay, previously entered numerical values are left shifted by six spaces in the display unit, and the selected concentration units are stored in the rightmost six spaces. The concentration unit is stored in system memory.

Data reduction keys 237 are used to let the user select a data reduction mode in the event that automatic data reduction selection is not desired.

ENTER key 240 is used to enter assay parameter and standard values in system memory. After an assay parameter or standard value has been keyed into the display using numeric keys 230 and concentration keys 235, it may be entered to memory by depressing ENTER key 240. This causes the display value to be entered into memory and printed. This also has the effect of incrementing the memory location pointer so that the next memory storage location becomes available for another value to be keyed in and entered. The ENTER key is also used to access memory locations for modification of values or clearing of a location which is to be deleted.

RUN key 242 is used to command the system to begin loading of standards and/or samples. Pressing this key after entry of all standards causes the system to display the instruction "LOAD STANDARDS" and pressing the key again causes the system to begin aspirating and counting standards and samples. If the system is halted during the assay by use of the numeric "1" key, the run may be continued by pressing RUN key 242.

PUMP key 245 provides a start/stop function for pump 58. One press of the key starts the pump, a second press stops the pump. This key is used to run the pump for the purpose of flushing the system.

FEED key 247 causes the printer to feed the paper forward when the key is depressed to enable the user to format the printout.

Having described the above key functions provided by the system software, the operation of the instrument during a standard assay procedure may now be understood. Initially, test tubes containing the standards and the samples to be assayed are loaded into the sample holder for subsequent sequencing. In particular, the samples are loaded so that the standards are measured first for calibration, and the samples to be assayed are measured next. During the initialization, the message "ENTER PRECISION" is displayed on display 22. The operator responds to this prompt by entering via numeric keys 230 the desired allowable percentage deviation of replicates from one another. After the desired value has been keyed in, the operator pushes ENTER key 240, at which point the system prints out the entry and provides an "ENTER # REPLICATES" prompt. The operator responds by keying in either 1 or 2 which will cause samples to be calculated singly or in pairs where pairs of samples are treated as duplicates so that their agreement may be checked. The operator then presses ENTER key 240, and is provided with an "ENTER STANDARD" prompt.

In response to the "ENTER STANDARD" prompt on display 22, the operator enters the concentrations of the standards into system memory in the order in which they were loaded onto the sample holder. Each concentration is keyed in, and upon verifying the entry on the display, the operator presses "ENTER" key 240 to store the value in memory and increment the memory pointer. A maximum of 16 standard entries is typical. Upon entry of a given standard concentration, the entry is printed out as it is stored, so that after all standards are entered, the operator may check the print out to ensure that the values are correct. The system provides the operator with the ability to correct an incorrect entry.

After the operator has entered and verified all standard concentrations, he presses RUN key 242 in response to which display 22 provides a "LOAD STANDARDS" prompt. The operator verifies that the first test sample (in container 50) of the standard set communicates with intake tubing 44 and upon verification, presses RUN key 242 again. The system now aspirates and counts all of the standard samples. After counting the fluorescence from the standards, the system prints out the concentrations and corresponding counts for all standards. In the event that non-automatic data reduction is desired, the operator halts the system by depressing and holding the numeral "1" key during the print out. In this mode, the operator then selects one of the four data reduction routines by depressing one of data reduction keys 237 corresponding to the four routines.

In general, the routine giving the highest correlation value should be used. The operator may eliminate a bad standard sample from the calculation by modifying the memory locations to zero out the concentration of the standard to be eliminated. If automatic data reduction is desired, the system automatically performs the data reductions by running the reciprocal, hyperbolic, and logit-log routines and determining which provides the highest correlation coefficient.

After the calibration parameters have been determined, the system aspirates and counts the samples sequentially as above discussed, and subsequently prints out the counts, the sample number, and the calculated sample concentration for each sample.

With respect to the second subset of the system software relating to data reduction procedures, such software provides the capability for microprocessor 130 to run in tandem with arithmetic processor 145 to execute standard curve fitting routines and calculate and evaluate results. In all, four curve fitting procedures are available—namely reciprocal, hyperbolic, logit-log, and linear interpolation. In all cases, the routine has as input a set of points $[(u_i, v_i)\ i=1,n]$ where $u_i$ is the concentration of the $i^{th}$ standard sample and $v_i$ is the number of counts for the $i^{th}$ standard sample.

In each of the first three procedures, the data is transformed to a new set of data points $[(x_i, y_i)\ i=1,n]$ and a least-squares fit of the transformed data to the functional form $y = Ax + B$ is carried out. This is a straight line of slope A and intercept B. The slope A, the intercept B and the correlation coefficient R are calculated as follows:

$$A = \frac{\overline{(xy)} - (\overline{x})(\overline{y})}{\overline{(x^2)} - (\overline{x})^2}$$

$$B = (\overline{y}) - A(\overline{x})$$

$$R = \left[ \frac{[\overline{(xy)} - (\overline{x})(\overline{y})]^2}{[\overline{(x^2)} - (\overline{x})^2][\overline{(y^2)} - (\overline{y})^2]} \right]^{\frac{1}{2}}$$

where:

$$\overline{x} = \frac{1}{n} \sum_{i=1}^{n} x_i$$

$$\overline{y} = \frac{1}{n} \sum_{i=1}^{n} y_i$$

$$\overline{(x^2)} = \frac{1}{n} \sum_{i=1}^{n} x_i^2$$

$$\overline{(y^2)} = \frac{1}{n} \sum_{i=1}^{n} y_i^2$$

$$\overline{(xy)} = \frac{1}{n} \sum_{i=1}^{n} x_i y_i$$

For the reciprocal procedure, the transformation is:
$x_i = u_i$
$y_i = 1/v_i$
so that the relationship between concentration u and counts v is $1/v = A\ u + B$.

For the hyperbolic procedure, the transformation is:
$x_i = \ln u_i$ $y_i = \ln v_i$ so that the relationship between concentration u and counts v is $\ln v = A \ln u + B$, or equivalently, $v = C u^A$ where $\ln C = B$.

For the logit-log procedure, the transformation is:

$$x_i = \ln u_i$$

$$y_i = \text{logit}(v_i/b_0)$$

$$= \ln \frac{v_i}{b_0 - v_i}$$

where $b_0$ is the count for a zero dose. Thus, in order to execute this procedure, a zero standard ($b_0$) must be entered and counted. The zero standard counts must be greater than the counts for the other standards and samples in the set. If a given standard sample has counts greater than $b_0$ (the zero standard), the point will be eliminated from the standard's data automatically. In the event that a sample being assayed gives counts greater than $b_0$ and logit data reduction is being used, the sample will be flagged and the display will show "UNDER RANGE".

Once a given curve has been fitted, the calculated values of concentration are calculated using the curve fit parameters. A check on standard curve validity is accomplished by requiring the computed correlation coefficient to exceed some prescribed minimum. If this condition is not met, the system will halt all operations.

It can thus be seen that the goodness of the fit depends on how well the particular transformation linearizes the data. While the above three procedures provide very good fit for many types of assay, there are certain situations where the transformed data points do not fit a straight line to the required precision. In such a situation, the operator may instruct the computer to use a linear interpolation procedure in which the curve is fitted is a sequence of straight line segments joining adjacent points. Such a fit is not actually a fit since the curve is guaranteed pass exactly through all the data points.

After the particular data reduction routine to be applied to the samples has been determined (automatically on the basis of the highest correlation coefficient, or manually by the operator), the slope and intercept parameters for the selected routines are computed and stored in memory. Thereafter, when samples are assayed and their counts determined, concentrations are calculated using these parameters.

We claim:

1. A fluorescence immunoassay apparatus for quantitating relatively small amounts of a clinically significant composition comprising:
   transparent means including a member constructed of a transparent material and defining therein a hollow cell for holding a liquid sample including fluorescent particles;
   means for flowing the sample into and out of the cell including an inlet to and an outlet from the cell;
   a sample probe;
   intake tubing fluidly communicating the probe with the inlet;
   discharge tubing fluidly communicating the outlet with a sample discharge point;
   a pump located downstream of the outlet for intermittently flowing a sample from the probe to the cell, for maintaining the sample in the cell for a period of time, and for thereafter removing the entire sample from the cell and the intake tubing and replacing the removed sample with a fresh sample;
   whereby the sample is not subjected to the flow inducing action of the pump until after it has passed the cell;
   a light source for generating a stable light beam focused on the sample;
   whereby the light beam causes fluorescent emissions by the particles in the sample, the intensity of which emissions is a function of the intensity of the light beam and the quantity of fluorescent particles in the sample; and
   means in optical communication with the transparent means for detecting photons resulting from fluorescent emissions by the particles when excited by the light beam;
   whereby the number of photons detected by the photon detecting means is a function of the number of fluorescent particles in the sample.

2. Apparatus according to claim 1 wherein the member has a plurality of mutually perpendicular outer surfaces, one of the surfaces facing the light source and being perpendicular to the light beam.

3. Apparatus according to claim 2 wherein the photon detecting means is positioned to receive fluorescent emissions from the particles in a direction perpendicular to the light beam; and wherein a second surface of the member perpendicular to the first mentioned surface is also perpendicular to the fluorescent emissions received by the photon detecting means.

4. Apparatus according to claim 3 wherein the photon detecting means includes a photomultiplier and lens means optically upstream of the tube for focusing the fluorescent emissions on a predetermined portion of the photomultiplier.

5. A fluorescence immunoassay apparatus for quantitating relatively small amounts of a clinically significant composition comprising:
   transparent means for holding a liquid sample including fluorescent particles;
   a light source for generating a stable light beam focused on the sample;
   whereby the light beam causes fluorescent emissions by the particles in the sample, the intensity of which emissions is a function of the intensity of the light beam and the quantity of fluorescent particles in the sample;
   means in optical communication with the transparent means for detecting photons resulting from fluorescent emissions by the particles when excited by the light beam, said photon detecting means including signal pulse generating means including a photomultiplier emitting individual signal pulses for sensed photons, and discriminator means for eliminating from the output of the photomultiplier noise pulses having a relatively lesser amplitude and generated by background noise; and
   whereby the number of photons detected by the photon detecting means is a function of the number of fluorescent particles in the sample.

6. Apparatus according to claim 4 or 5 including a cutoff filter optically upstream of the photomultiplier for blocking the light wavelength with which the fluorescent particles in the sample are excited from reaching the photomultiplier.

7. Apparatus according to claim 6 including an interference filter optically upstream of the photomultiplier for removing from light received by the photomultiplier substantially all light having a wavelength other than the wavelength of fluorescent emissions.

8. Apparatus according to claim 1 or 5 including stabilizing means for preventing the intensity of the light beam generated by the light source from varying by more than a predetermined amount.

9. Apparatus according to claim 8 wherein the stabilizing means includes a power supply for the light source, means for sensing the intensity of the beam, and circuit means operatively coupled with the sensing means and the power supply for adjusting the output of the power supply in response to changes in the intensity of the light beam so that the light beam intensity remains substantially constant.

10. Apparatus according to claim 9 wherein the sensing means comprises a photodiode, and wherein the circuit means includes means for amplifying an output of the photodiode, means for comparing the amplified output of the photodiode with a reference signal to generate a difference signal, and means for applying the difference signal to the power supply to correspondingly adjust its output to the light source.

11. Apparatus according to claim 10 wherein the light source comprises a tungsten-halogen incandescent lamp and the photodiode comprises a silicon photodiode.

12. Apparatus according to claim 10 including filter means between the light source and the sample for conditioning the light beam so as to minimize light scattering and enhance fluorescent emissions by the particles, and wherein the photodiode is positioned relatively proximate to the transparent means and optically downstream of the filter means.

13. Apparatus according to claim 10 wherein the circuit means maintains the intensity of the light beam within one percent of a reference intensity.

14. Apparatus according to claim 5 wherein the transparent means comprises a member constructed of a transparent material and defining therein a hollow cell, and including means for flowing the sample into and out of the cell.

15. Apparatus according to claim 1 or 14 including a band pass filter disposed in the light beam optically upstream of the member for removing from the light beam substantially all light other than light having a wavelength which excites the particles and generates fluorescent emissions.

16. Apparatus according to claim 15 wherein the band pass filter eliminates substantially all light from the light beam having a wavelength other than 490 nanometers.

17. Apparatus according to claim 14 wherein the flowing means comprises an inlet to and an outlet from the cell, and further including a sample probe, intake tubing fluidly communicating the probe with the inlet; discharge tubing fluidly communicating the outlet with a sample discharge point, and a pump located downstream of the outlet for intermittently flowing a sample from the probe to the cell, for maintaining the sample in the cell for a period of time, and for thereafter removing the entire sample from the cell and the intake tubing and replacing the removed sample with a fresh sample; whereby the sample is not subjected to the flow inducing action of the pump until after it has passed the cell.

18. Apparatus according to claim 1 or 17 wherein at least the discharge tubing comprises resiliently flexible tubing, and wherein the pump comprises a peristaltic pump.

19. Apparatus according to claim 1 or 17 wherein the intake tubing comprises polytetrafluoroethylene tubing.

20. Apparatus according to claim 1 or 17 including first and second containers for holding samples, and including means for alternatively fluidly communicating the sample probe with the containers.

21. Apparatus according to claim 20 wherein the first container includes a rinse solution; and means for alternatingly fluidly communicating the sample probe with the first and second containers in response to each operation of the pump so that at least the intake tubing and the cell is cleaned with the rinse solution after the withdrawal of a sample from the intake tubing and the cell and prior to the replacement of the sample with the fresh sample.

22. Apparatus according to claim 1 wherein the photon detecting means includes means for generating signal pulses for individually sensed photons.

23. Apparatus according to claim 22 wherein the signal pulse generating means comprises a photomultiplier emitting individual signal pulses for sensed photons, and discriminator means for eliminating from the output of the photomultiplier noise pulses having a relatively lesser amplitude and generated by background noise.

24. Apparatus according to claim 23 or 5 wherein the discriminator means comprises a source of a reference signal having a lesser amplitude than the signal pulses, and comparing means receiving as an input the pulses and the reference signal and generating an output signal from which pulses having an amplitude which is less than that of the reference signal have been eliminated.

25. Apparatus according to claim 24 wherein the amplitude of the reference signal is at least about as large as the amplitude of the majority of noise pulses.

26. Apparatus according to claim 25 wherein the amplitude of the reference signal exceeds the amplitude of the noise signals.

27. Apparatus according to claim 22 or 5 including digital pulse counting means having an input in communication with the signal pulse generating means for producing a numeric code representative of the number of pulses received at the input.

28. Apparatus according to claim 27 wherein the pulse counting means includes an enable input, and further including processor means coupled to the pulse counting means, the processor means having means for receiving and storing the numeric code from the pulse counting means, the processor means also having means for enabling the pulse counting means for a predetermined interval of time so that the numeric code stored is representative of concentration of the clinically significant compound.

29. Apparatus according to claim 28 wherein the processor includes means for storing the known concentrations of the clinically significant compound for a plurality of standard samples, means for storing a corresponding plurality of numeric codes corresponding to the measured fluorescent activity of the plurality of samples having known concentration, and arithmetic means for computing a calibration curve on the basis of the plurality of known concentrations and the plurality of numeric codes.

30. Apparatus according to claim 29 wherein said arithmetic means includes means for computing a calibration curve according to at least two mathematical hypotheses, and for choosing the mathematical hypothesis that provides the highest correlation coefficient.

31. Apparatus according to claim 22 or 5 and further comprising:
  digital pulse counting means for receiving the signal pulses from said photon detecting means and for providing a numeric code output representative of the number of pulses counted;
  programmed microcomputer means in communication with the pulse counting means, the programmed microcomputer means having means for selectively enabling the counting means for a predetermined time interval such that the numeric code from the counting means is representative of the concentration of the clinically significant compound, the microcomputer means having means for storing known concentration information for a plurality of standard samples and means for accumulating and storing count information corresponding to said plurality of standard samples, the microcomputer having means for determining a calibration curve on the basis of the known concentrations and count information according to at least two mathematical hypotheses and for selecting the calibration curve that provides the best correlation coefficient.

32. Apparatus according to claim 31 and further comprising means for interfacing the microcomputer means to a remote computer for remote data logging.

33. A fluorescence immunoassay apparatus for quantitating relatively small amounts of a clinically significant composition comprising: flow means including a transparent housing defining an interior cell and an inlet and an outlet to and from the cell, respectively, for flowing a fluid sample including fluorescent particles in individual batches through the cell and for holding a portion of each batch for at least a minimum period of time stationarily in the cell; optical means including a light source generating a light beam which is directed into the cell for causing fluorescent emissions by the particles in the cell, the intensity of which is a function of the intensity of the light beam and the quantity of particles in the cell; photosensing means for sensing the fluorescent emissions over a predetermined time period and for generating corresponding output signals; means for stabilizing the intensity of the light beam to prevent variations in the intensity of the light beam in excess of about one percent from a preset light beam intensity; discriminator means for eliminating from the output signals at least a substantial portion of any background noise signals which are included in the output signals; and processing means responsive to the output signals for quantitatively identifying the fluorescent emissions to thereby measure the number of particles present in the cell.

34. Apparatus according to claim 33 including means defining a generally L-shaped optical chamber having perpendicular optical axes; and wherein the cell is disposed at the intersection of the axes.

35. Apparatus according to claim 33 wherein the optical means and the photosensing means are disposed in the optical housing and aligned with the first and second optical axes, respectively.

36. Apparatus according to claim 35 wherein the transparent housing has a generally square cross-section, the housing including first and second perpendicular sides which are arranged perpendicular to the first and second optical axes, respectively.

37. Apparatus according to claim 36 wherein the cell has a square cross-section and includes first and second perpendicular walls which are parallel to the first and second sides of the housing.

38. Apparatus according to claim 33 wherein the photosensing means comprises a photomultiplier tube, wherein the output signals comprise signal pulses generated by photons from fluorescent emissions of the particles in the cell and noise pulses; and wherein the discriminator means includes means for eliminating the noise pulses from the output signals before the signal pulses are fed to the processing means.

39. Apparatus according to claim 38 wherein the signal pulses have an amplitude greater than the noise pulses, and wherein the discriminator means includes an amplitude discriminator for eliminating the noise pulses from the output signals.

40. Apparatus according to claim 33 including pump means in fluid communication with the outlet and disposed downstream of the cell, and means for intermittently activating the pump means to flow the sample out of the cell and to flow a fresh sample into the cell.

41. Apparatus according to claim 33 wherein the processing means includes digital counting means, and microcomputer means for receiving and storing numeric information from the counting means, the microcomputer means having means for enabling the counting means for a predetermined length of time so that the numeric information is representative of the number of particles in the cell.

42. Apparatus according to claim 41 wherein the microcomputer means has means for enabling the pump activating means at a time when the counting means is not enabled so that counting may occur while the sample is stationary in the cell.

43. Apparatus according to claim 41 wherein the microcomputer means includes means for storing known concentration information for a plurality of standard samples and means for accumulating and storing count information corresponding to said plurality of standard samples, the microcomputer having means for determining a calibration curve on the basis of the stored known concentrations and count information according to at least two mathematical hypotheses and for selecting the calibration curve that provides that best correlation coefficient.

44. A fluorescent immunoassay apparatus for quantitating relatively small amounts of a clinically significant composition comprising: flow means including a transparent housing having a square cross-section and including an interior sample cell of a square cross-section corresponding housing sides and cell walls being parallel to each other, the housing including an inlet to and an outlet from the cell; an intake conduit in fluid communication with the inlet and having an other end; means for alternatingly connecting the other end of the intake conduit with a container holding a fluid sample including fluorescent particles and a second container holding a rinsing fluid; a discharge conduit in fluid communication with the outlet; pump means disposed downstream of the outlet and cooperating with the discharge conduit; means for intermittently activating the pump means to flow a fluid by suction through the intake conduit, the cell and a portion of the discharge conduit and for flowing the fluid to a point of discharge; sequencing means for intermittently activating the pump means and for alternatingly connecting the intake conduit with the first and second containers to alternatingly flow sample fluid and a rinsing fluid into the cell; the sequencing means including means for activating the pump means for a sufficient length of time to evacuate the entire fluid in the cell and replace it with fresh fluid from one of the containers;

an optical housing defining a pair of perpendicular, optical branches defining perpendicular optical axes, the cell being disposed in the optical housing and at an intersection of the axes; a light source in one of the branches for generating a light beam and first optical means disposed in the optical branch between the light source and the cell for removing from the light beam substantially all light other than light of a wavelength which causes the fluorescent particles to emit fluorescent emissions; a photomultiplier in the other branch and second optical means for directing the fluorescent emissions onto the photomultiplier, the photomultiplier generating a signal pulse for each fluorescent transmission photon received thereby and noise signals; the housing including means for preventing light other than fluorescent emissions caused by the direct excitation of the fluorescent particles by the light beam from reaching the photomultiplier;

light beam stabilization means operatively coupled with the light source and including a photosensor disposed in the optical housing proximate the transparent housing and optically downstream of the first optical means for sensing the light beam striking the housing and for adjusting its intensity so that the light beam remains substantially constant;

discriminator means operatively coupled with the photomultiplier for removing the noise signals and for generating output signals comprising substantially only signal pulses;

counting means operatively coupled with the discriminator means for counting the number of signal pulses emitted by the photomultiplier; and microcomputer means having means for enabling the counting means over a predetermined, constant length of time and for forming an output which is an indication of the number of fluorescent particles in the sample cell, the microcomputer means having means operatively coupled with the pump means for deactivating the pump means during at least the predetermined length of time and for activating the pump means during other times so that a tested sample fluid from the cell is removed, the cell is rinsed with rinsing fluid, and thereafter a fresh sample fluid is flowed into the cell.

* * * * *